United States Patent [19]

Pratt, Jr.

[11] E Patent Number: Re. 32,782

[45] Reissued Date of Patent: Nov. 15, 1988

[54] METHOD FOR DETERMINING IN VIVO, BONE STRENGTH

[75] Inventor: George W. Pratt, Jr., Wayland, Mass.

[73] Assignee: Massachusetts Institute of Technology, Cambridge, Mass.

[21] Appl. No.: 811,864

[22] Filed: Dec. 20, 1985

Related U.S. Patent Documents

Reissue of:

[64] Patent No.: 4,421,119
Issued: Dec. 20, 1983
Appl. No.: 329,932
Filed: Dec. 11, 1981

U.S. Applications:

[60] Division of Ser. No. 48,580, Jun. 15, 1979, Pat. No. 4,361,154, which is a continuation-in-part of Ser. No. 928,654, Jul. 28, 1978, Pat. No. 4,233,845.

[51] Int. Cl.[4] ..... A61B 10/00

[52] U.S. Cl. ..... 128/660.06; 128/774; 73/597

[58] Field of Search ..... 128/660, 774; 73/597, 73/598, 632

[56] References Cited

U.S. PATENT DOCUMENTS

| | | | |
|---|---|---|---|
| 2,439,130 | 4/1948 | Firestone | 73/67 |
| 3,345,863 | 10/1967 | Henry | 73/67.5 |
| 3,477,422 | 11/1969 | Jurist et al. | 128/2 |
| 3,664,180 | 5/1972 | McDonald et al. | 73/67.6 |
| 3,711,129 | 1/1973 | Munger | 73/67.9 |
| 3,847,141 | 11/1974 | Hoop | 128/2 V |
| 4,048,986 | 9/1977 | Ott | 128/2 R |
| 4,138,999 | 2/1979 | Eckhart et al. | 128/2 V |

FOREIGN PATENT DOCUMENTS

| | | | |
|---|---|---|---|
| 2318420 | 2/1977 | France . | |
| 619841 | 2/1959 | U.S.S.R. . | |
| 219853 | 9/1968 | U.S.S.R. | 73/598 |

OTHER PUBLICATIONS

"The Role of Collagen in the Elastic Properties of Calcified Tissues", Lees, S. and Davidson, C. Journal of Biomechanics, vol. 10, No. 7, 1977, pp. 473–486.

"Measurement of Ultrasound Velocity in Human Tissue", Van Venrooij, G., Ultrasonics, Oct. 1971, pp. 240–242.

"Comparison of Two Formulae In Vivo Prediction of Strength of the Femur", Mather, B.S. Aerospace Medicine, vol. 38, No. 12, 12/67, pp. 1270–1272.

"Ultrasonic Technique for the Evaluation of Bone Fractures" Anast, G. T., Fields and Siegel, I. M., pp. 157–159.

Physical Principles of Ultrasonic Diagnosis, Wells, P. N. T., Academie Press; London 1969, pp. 1–27.

"Ultrasonic and Selected Physical Properties of Bone", Abendschein, W. and Hyatt, G. W., Apr. 1970, pp. 294–301.

"Ultrasonic Assessment of Early Callus Formation", Brown, S. A. and Mayor, M. B., Biomedical Engineering, vol. 11, No. 4, Apr. 1976, pp. 124–128.

Strength of Biological Materials, Yamada, H., 1970, pp. 53–57.

"Ultrasonic Prediction of Delayed or Nonunion of Fractures", Mayor, M. B. and Brown, S. A., Proceedings of the Fifth New England Bioengineering Conference, Apr. 15, 1977, pp. 229-233.
"Sing-Around Ultrasonic Velocimeter for Liquids", Greenspan, M. and Tschiegg, C., The Review of Scientific Instruments, vol. 28, No. 11, 11/57, pp. 897-901.
"The Investigation of Bone's Substructure Using Megahertz Sound and a Porous Model", Martin, B. and Haynes, R. and ASME Publication, Dec. 3, 1970.
"Ultrasonic Method for Measuring Elastic Coefficients of Bone and Results on Fresh and Dried Bovine Bones", IEEE Transactions on Bio Medical Engrg., vol. BME-17, No. 2, Apr., 1970, pp. 101-105, by Lang, S.
"Preventive Diagnosis of Breakdown" by Okumura, Massachusetts Institute of Technology, May 1978.

*Primary Examiner*—Lee S. Cohen
*Attorney, Agent, or Firm*—Hale and Dorr

[57] ABSTRACT

A system for establishing, in vivo, the strength of bone in a live being such as, for example, a horse. The system permits determination of the speed of travel of sound through the bone and the strength of the bone is assessed on the basis of said speed of travel.

* * * * *

The questions raised in reexamination request No. 90/000,815, filed 07/22/85, have been considered and the results thereof are reflected in this reissue patent which constitutes the reexamination certificate required by 35 U.S.C. 307 as provided in 37 CFR 1.570(e).

6 Claims, 1 Drawing Sheet

METHOD FOR DETERMINING IN VIVO, BONE STRENGTH

Matter enclosed in heavy brackets [ ] appears in the original patent but forms no part of this reissue specification; matter printed in italics indicates the additions made by reissue.

This is a division of application Ser. No. 048,580 filed June 15, 1979 (now U.S. Pat. No. 4,361,154) which was a continuation-in-part of Ser. No. 928,654, filed July 28, 1978 (now U.S. Pat. No. 4,233,845).

The present invention relates to mechanisms for determining the strength of bone and the condition of tendons and ligaments of a live being.

In the explanation that follows, most attention is directed to the study of horses, particularly since work leading to the present invention was done in connection with horses.

When bone is stressed in a succession of load-unload cycles an accumulation of microscopic damage occurs if the peak load per unit area is sufficiently high. Chamay (A. Chamay, J. Biomechanics 3, 263 (1970)) has described this process as repeated strain in the "fatigue zone". Slow bone deformation is observed, the bone not returning after unloading at the end of a cycle to its precise condition at the start of the cycle. Continual cycling in the fatigue zone eventually leads to fracture. This accumulation of internal damage is not unlike that taking place in a piece of metal when it is bent back and forth or flexed repeatedly. Micro-crushing and micro-fracturing occurs in bone in the process of absorbing shock. Given a period of rest the body restores the strength of bone in a remodeling process. It is important to understand that the bones in the skeletal structure that are subjected to large stresses are constantly going through fatigue weakening on the one hand and restoration by remodeling on the other.

The present invention is primarily concerned with a way of noninvasively determining the strength of bone in a live animal. The race horse in particular subjects his legs to very large stresses in the course of training and competition. Of every 1000 horses starting races between three and six horses will suffer a fracture and many of these animals will have to be destroyed. This represents an unfortunate loss of animal life and in many cases a severe economic loss. Although a horse may come out of a race in outwardly fine shape, there has been no method of accurately gauging how much subtle wear and tear has taken place. These problems of the horse are shared by other quadrupeds such as the racing greyhound dog and, of course, man himself.

It has been found and is herein disclosed that the strength of bone can be monitored by measuring the velocity of sound through the bone. As bone is weakened by repeated load cycling, it has been discovered that the velocity of sound continually decreases. Experiments have been carried out on the third metacarpal bone freshly removed from the leg of a horse. This work is described in a thesis "Preventive Diagnosis of Breakdown" by Kelvin O'Kamura (MIT library 1979) which was done under the present inventor's supervision. This disclosure takes these in-vitro experiments and extends the technique to bone in the living animal where the complication of surrounding soft tissue must be dealt with. Typical values of the velocity of sound at $0.5\times10^6$ Hz before load cycling were 2850 m/sec at the distal end, 3140 m/sec across the midshaft, and 2600 m/sec across the proximal end. Sample bones were load cycled using a Materials Testing Service (MTS) computer controlled hydraulic press. The computer controlling the action of the machine was programmed to apply a load to the cannon horse (Mc III) as a function of time in a manner that simulates the actual load cycle of the race horse in competition. The velocity of sound was measured across distal, midshaft, and proximal regions. It was found that the velocity of sound continually decreases as a result of cycling. The load cycling process ultimately produces a fracture of the bone. It was observed that the velocity of sound suffered the largest decrease in the region where the fracture later occurred. A drop in the velocity of sound of approximately 10% was found to take place due to the load cycling in the region of eventual fracture.

A linear relation between the elastic modulus E of horse and the density $\rho$ has been published by H. F. Schryver (Am. Journal of Vet. Res. 35, 25 (1978) in the form $$E=E_0+E_{1\rho}$$

Schryver further has published a linear relation between the breaking strength B and the density.

$$B=B_0+B_{1\rho}.$$

One can use these relations to demonstrate a relation between breaking strength B and the velocity of sound v. Since $v=\sqrt{E/\rho}$ it can be shown that the above equations yield $$B = B_0 + \frac{E_0 B_1}{v^2 - E_1}$$

Using the values of $B_0$, $B_1$, $E_0$ and E, given by Schryver, it is found that a 15% change in velocity of sound corresponds to a 40% change in breaking strength. Therefore, the observations made and disclosed here relating the strength of horse to the velocity of sound are supported by other work on the properties of bone. The link between velocity of sound and bone strength and the required conditions to observe sound propagation in-vivo are first disclosed herein.

It was found for present purposes that damping of ultrasonic propagation was so severe at $2\times10^6$ Hz and at higher frequencies that these frequencies could not be used for a noninvasive measurement of bone strength. Successful experiments were carried out at 500 KHz and 1 MHz. Both acoustic transmission and echo modes are utilized.

Cheney et al ("Cannon bone fracture in the thoroughbred racehorse," Med. Biol. Eng. 4:613–620 (1973)) have shown that the force on the cannon bone of a horse may be three to four times the force on the hoof on the ground due to the lever-type action of the fetlock joint. Under a single loading, the breaking strength of the cannon bone in vitro is approximately $71\times10^3$N. The present model suggests peak forces in the range of $11\times10^3$N on the hoof, which translates to $33\times10^3$N on the cannon bone. However, Cheney et al have found that repeated loading reduces the strength of the cannon bone by some 40% over a period of 4,000 cycles, which could be produced by 10 races. Similar results have been observed in the tibia of living rats. If this were true of the living system, the breaking strength could drop to $43\times10^3$N, which is very close to the forces expected from the present model. In the living system, there is a tendency to strengthen bone in the regions of greatest stress. The fatigue weakening of the bone takes place over a much shorter period than that required for the strengthening process to occur. Consequently, if sufficient recovery time is not allowed for a horse that runs at speeds exceeding his safe speed for a great part of the time, then his supporting bones can be expected to drop in strength to the point where the normal loads experienced in racing will cause fracture. The elastic modulus of bone is known to decrease as it weakens as a result of cyclic loading. The present inventor has discovered that this process can be monitored in the live animal by measuring the velocity of sound across the leg. Measurements on the metacarpal and metatarsal bones at 0.5 MHZ and 1 MHz, indicate a drop in sound speed across the proximal, distal and midshaft portions of said bones. A drop by 10 percent has been found to exhibit a high correlation with subsequent fracture.

Accordingly, it is an object of the present invention to provide a system for relating the rate of travel of acoustic energy through a bone with the strength of that bone.

Another object is to provide a mechanism to permit in vivo determination of bone strength.

Still another object is to provide a mechanism which permits determination in vivo, of the strength (and changes therein) of leg bones of a quadruped in particular the horse.

These and still further objects are addressed hereinafter.

The foregoing objects are achieved, generally, in apparatus and method for establishing, in vivo, the strength of a bone (or the condition of tendons, ligaments or the like) that comprises a system for launching an elastic or acoustic pulse through the bone, determining the speed of propagation of the elastic or acoustic energy through the bone and relating the speed of propagation to the strength of the bone.

The invention is hereinafter described with reference to the accompanying drawing in which.

Figure 1:
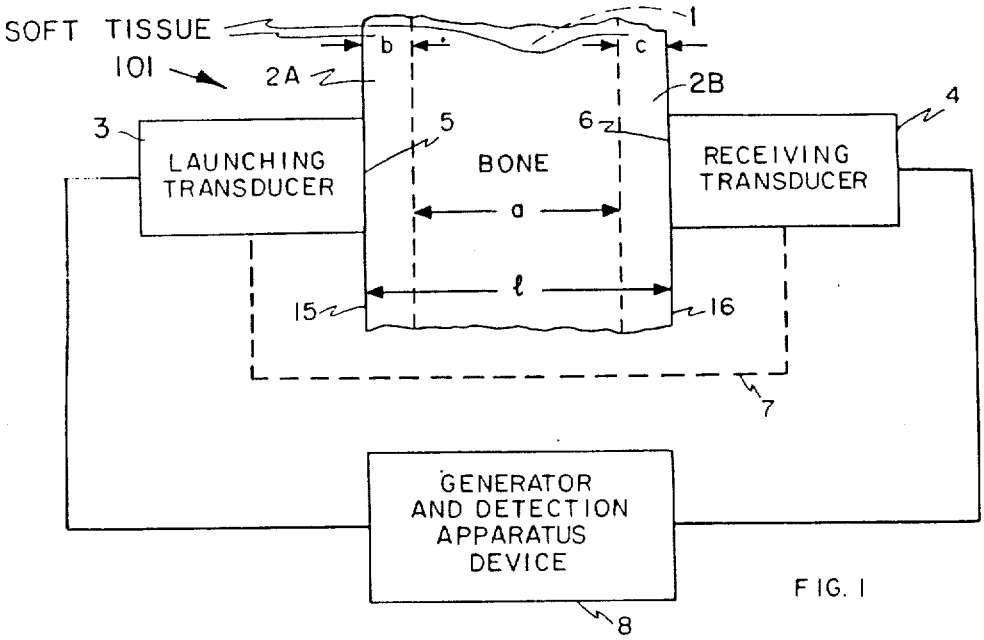
FIG. 1 is a diagrammatic representation of apparatus to measure the speed of elastic energy in a bone (or tendons or ligaments), in vivo, and shows, diagrammatically a side view of a representation of a portion of a leg of a horse.

Turning now to FIG. 1, apparatus to which the general designation 101 is applied serves to establish, as later discussed in detail, the mechanical strength of a member 1 (which may be a leg bone of a horse, for example, but may also be a tendon or ligament, as later discussed). The bone 1 is surrounded by soft tissue which, for purposes later in this explanation, is labeled 2A and 2B to designate, in FIG. 1, tissue at the left of the bone 1 and tissue at the right of the bone 1, respectively. As is noted elsewhere herein, experiments by the present inventor have shown that a substantial change in the elastic properties of the bone 1 affects the transmission speed of sound therethrough. Accordingly, the present inventor determines the speed of sound through the bone and relates that speed and changes therein to the strength of the bone.

Figure 2:
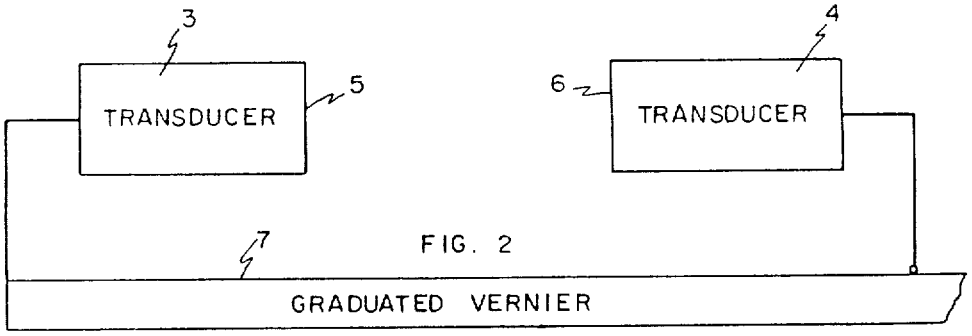
FIG. 2 shows, diagrammatically, a portion of the apparatus of FIG. 1.

Toward this end, the apparatus 101 includes a launching transducer 3 (also called "first transducer means" herein) having a launching surface 5 and a receiving transducer 4 (also called "second transducer means" herein) having a receiving surface 6. The transducers 3 and 4 are mechanically interconnected by a graduated vernier represented by the broken line marked 7 in FIG. 1 and shown also in FIG. 2. A generation and detection device 8 energizes the transducer 3 to launch an acoustic pulse and receives signals from the transducer 4 when the pulse is received. The device 8 can calculate overall transit time of the acoustic pulse through the bone and surrounding tissue. The present inventor has found that the apparatus 101 can be employed in a number of ways, as now discussed.

In the live animal, one does not have direct, non-invasive access to the bone. The technique used here is to launch a sound pulse using the launching or sending transducer 3 in FIG. 1 at the surface 15 of the skin of the animal in FIG. 1. This pulse is detected either at another site such as 16 in FIG. 1 on the surface of the leg as a transmitted signal or is detected at the same site 15 as an echo signal, as later noted. Vaseline or other coupling agent is used to effectively couple the sound energy into the leg. It has been found that a useful measure of the local strength of the leg in-vivo is the effective velocity of propagation through the path starting at the site of the sending transducer through first a covering layer of coat, skin and soft tissue; second the bone itself; and finally the covering layer of coat, skin, and soft tissue at the site of a pick up transducer 4. The sending and pick-up transducers are held in the vernier apparatus 7 in FIG. 2 that determines the distance between the transducers 3 and 4. In practice the horse is used as his own control and the effective velocity, defined as the distance between sending and pick up transducers divided by the propagation time, is used as a comparative measure of local bone strength. By comparing the effective velocities for corresponding regions of the two forelegs or two hind legs, a measure of condition is obtained. It has been found that the effective velocities of sound agree between corresponding sites on a pair of legs to within 1% in normal legs. In abnormal conditions, the effective velocities have been found to be as much as 10% different. In that case, the leg with the lower effective velocity of sound reading has become weakened and there is a danger of severe injury.

Instead of working with the effective velocity, it is possible to determine the actual velocity through the bone by a combination of transmission and echo experiments. First, a transmission measurement is made to determine the effective velocity i.e., the total transmission time t required for a sound pulse to travel from the launching transducer 3 in FIG. 1 at the skin surface 15 to the skin surface 16 where it is picked up by the receiving transducer 4. The graduated vernier 7 in FIG. 2 measures the total transit distance l between surfaces 15 and 16 of FIG. 1. This measured distance l is the sum of the distances a, b and c shown in FIG. 1, i.e., $$l=a+b+c$$

Figure 3:
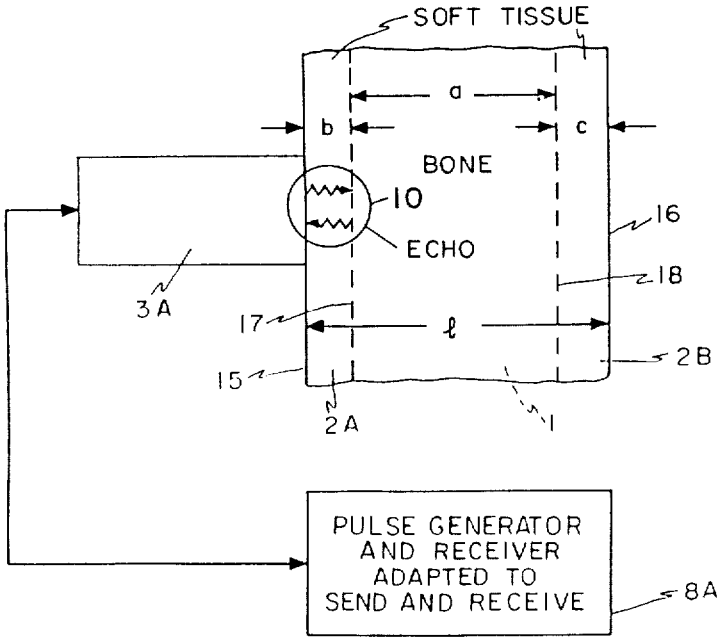
FIG. 3 shows, diagrammatically, a modification of the apparatus of FIG. 1.

Secondly, echo experiments are made as shown in FIG. 3 at the surfaces 15 and 16 of the leg. A send and receive transducer as 3A in FIG. 3, energized by a pulse generator and receiver 8A, launches an acoustic pulse through the coat and soft tissue 2A of depth b in FIG. 3. This pulse is reflected from the surface 17 of the bone and an echo in FIG. 3 returns to the transducer 3A (at surface 5A) where it is picked up. The time $t_1$ required for the echo to arrive at transducer 3A is measured. The speed of sound at 1 MHz through the soft tissue of path-length in b FIG. 3 is approximately 1570 meters/sec. Denoting this speed as $v_t$, the distance b in meters is given by $$b = \frac{1570\, t_1}{2} \text{ meters}$$

Repeating this echo experiment at the site 16 where the receiving transducer 4 has been positioned, results in measuring a second echo time $t_2$ and a determination of the path-length c in FIG. 3:

$$c = \frac{1570\, t_2}{2} \text{ meters}$$

The outgoing acoustic pulse and the reflected or echo acoustic pulse in FIG. 3 are indicated by the arrows within the circle marked 10. It should be further noted at this juncture that the transducer 3A can be like the transducers 3 and 4 which can send and receive and the device 8 can be made to interpret both.

The path length a through the bone in FIG. 3 is the measured distance l less b+c. The propagation time $t_b$ through the bone is the total transmission time t defined above less $(t_1+t_2)/2$. Hence, the speed of sound through the bone alone denoted by $v_b$ is $$v_b = \frac{l - 785\,(t_1 + t_2)}{t - 0.5\,(t_1 + t_2)}$$

Measurements of the effective velocity of sound through various parts of the leg or measurements of the actual speed of sound through the bone have been successfully used in a comparative sense, i.e., comparing the sound speed through corresponding regions of a pair of legs. As explained above, differences of 5% or more between corresponding regions is an indication of relative weakness of the leg with the lower effective actual velocity. Not only can measurements be used in a comparative sense but in an absolute sense to measure bone strength. In particular, in young horses, e.g., two-year olds, one often encounters the condition of bucked shins. Microfracturing of the cannon bone creates a painful condition requiring the horse to be taken out of training. This microfracturing will be accompanied by a weakening of the bone and a decrease in the effective or actual speed of sound. This ultrasonic method can, therefore, be used to detect the onset of this condition.

Not only can the condition of bone be evaluated by measuring the velocity of sound through the bone but the condition of tendons, ligaments, and other soft tissue can also be determined. A condition known as bowed tendon is common in the horse. It is associated with an overstressing of the deep flexor and superficial flexor tendons. The overstressing leads to mechanical changes in the state of the tendon such as changes in alignment of tendon fibers and fluid invading the tendon structure. These changes will alter the speed and damping of an acoustic signal propagating in the tendon either in a transmission or echo mode. Observation of the speed and damping of the acoustic signal will give information about the condition of the tendon. Comparing the normal and overstressed tendon or ligament is an effective means of determining relative condition.

It has further been observed that the acoustic signal will not propagate across an actual macroscopic fracture. Failure to receive an acoustic signal at the receiving transducer from a sending transducer is a strong indication of actual fracture.

Further modifications of the invention herein disclosed will occur to persons skilled in the art and all such modifications are deemed to be within the scope of the invention as defined by the appended claims.

What is claimed is:

[1. Apparatus for establishing, in vivo, the strength of a bone member, that comprises, in combination:

a linear scale;

first transducer means having a sending surface to launch an acoustic pulse through the bone member;

second transducer means having a receiving surface to receive the pulse after transmission through the bone member, said receiving surface being parallel to and facing said sending surface so that said bone member may be positioned between and in contact with both of said surfaces;

said first and second transducer means being mechanically interconnected by said linear scale so that the distance between said sending surface and said receiving surface may be measured; and means for measuring the transit time of the pulse from the first transducer means to the second transducer means to permit determination of the velocity of the propagated signal through the bone.]

[2. The apparatus of claim 1 wherein said linear scale is a graduated vernier upon which said first and second transducer means are mounted.]

*3. A method for establishing, in vivo, the strength of a bone, that comprises the steps of:*

*a. providing:*

*(1) a linear scale;*

*(2) first transducer means having a sending surface to launch an acoustic pulse through a bone and surrounding soft tissue;*

*(3) second transducer means having a receiving surface to receive the pulse after transmission through a bone and surrounding soft tissue, said receiving surface being parallel to and facing said sending surface so that said soft tissue surrounding a bone may be positioned between and in contact with both of said surfaces;*

*(4) said first and second transducer means being mechanically interconnected by said linear scale so that the distance between said sending surface and said receiving surface may be measured; and*

*(5) means for measuring the transit time of the pulse from the first transducer means to the second transducer means to permit determination of the velocity of the propagated signal through a bone and soft tissue;*

*b. conducting the following steps (1)–(4) a first time:*

*(1) launching a pulse through a bone and surrounding soft tissue with said first transducer means;*

*(2) measuring the distance between said sending and receiving surfaces with said linear scale;*

*(3) measuring the transit time of the pulse from the first transducer means to the second transducer means with said means for measuring transit time and;*

*(4) determining the effective velocity of the pulse through said bone and surrounding soft tissue by*

*dividing the measured distance by the measured transit time;*

*c. conducting the steps (b.1) through (b.4) at least one additional time; and*

*d. comparing the effective velocity determined by conducting steps (b.1) through (b.4) the first time with the effective velocity determined by conducting steps (b.1) through (b.4) at least one additional time with respect to a bone at a location corresponding to the location at which the first pulse was launched through the bone through which the first pulse was launched; and*

*e. assessing the strength of the bone through which each pulse has been launched on the basis of the comparison.*

*4. The method of claim 3 further wherein the step of assessing the strength of the bone is made on the basis that a difference, between the effective velocity of the acoustic pulse launched through a bone and surrounding soft tissue and the effective velocity of an acoustic pulse launched at least one additional time through a corresponding location on a bone and surrounding soft tissue, of greater than about 5 percent indicates a weakness in the bone through which the acoustic pulse propagated at the lower effective velocity.*

*5. A method for establishing, in vivo, the strength of a bone that comprises the steps of:*

*a. providing:*

*(1) a linear scale;*

*(2) first transducer means having a sending surface to launch an acoustic pulse through a bone and surrounding soft tissue;*

*(3) second transducer means having a receiving surface to receive the pulse after transmission through a bone and surrounding soft tissue, said receiving surface being parallel to and facing said sending surface so that said soft tissue surrounding a bone may be positioned between and in contact with both of said surfaces;*

*(4) said first and second transducer means being mechanically interconnected by said linear scale so that the distance between said sending surface and said receiving surface may be measured; and*

*(5) means for measuring the transit time of the pulse from the first transducer means to the second transducer means to permit determination of the velocity of the propagated signal through a bone and soft tissue;*

*b. conducting the following steps (1)–(4) a first time:*

*(1) launching a pulse through a first bone and surrounding soft tissue with said first transducer means;*

*(2) measuring the distance between said sending and receiving surfaces with said linear scale;*

*(3) measuring the transit time of the pulse from the first transducer means to the second transducer means with said means for measuring transit time and;*

*(4) determining the effective velocity of the pulse through said bone and surrounding soft tissue by dividing the measured distance by the measured transit time;*

*c. conducting the steps (b.1) through (b.4) at least one additional time, with respect to a second bone at a location corresponding to the location at which the first pulse was launched through the first bone through which the pulse was launched; and*

*d. comparing the effective velocity determined by conducting steps (b.1) through (b.4) the first time with respect to said first bone with the effective velocity determined by conducting steps (b.1) through (b.4) the at least one additional time through said second bone; and*

*e. assessing the strength of the bone through which each pulse has been launched on the basis of the comparison.*

*6. The method of claim 5 further wherein the step of assessing the strength of the bone is made on the basis that a difference of greater than about five percent, between the effective velocity of the acoustic pulse launched through a bone and surrounding soft tissue and the effective velocity of an acoustic pulse launched at least one additional time through a corresponding location on a different bone and surrounding soft tissue, indicates a weakness in the bone through which the acoustic pulse propagated at the lower effective velocity.*

* * * * *